(12) United States Patent
Singh et al.

(10) Patent No.: US 8,710,218 B2
(45) Date of Patent: Apr. 29, 2014

(54) PROCESS FOR PREPARATION OF EFAVIRENZ

(75) Inventors: Girij Pal Singh, Pune (IN); Gurvinder Pal Singh, Pune (IN); Pravin Mahajan, Pune (IN); Ganesh Salunke, Pune (IN); Dabeer Karnalkar, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 209 days.

(21) Appl. No.: 13/383,645

(22) PCT Filed: Jul. 12, 2010

(86) PCT No.: PCT/IN2010/000465
§ 371 (c)(1),
(2), (4) Date: Jan. 12, 2012

(87) PCT Pub. No.: WO2011/007367
PCT Pub. Date: Jan. 20, 2011

(65) Prior Publication Data
US 2012/0108809 A1 May 3, 2012

(30) Foreign Application Priority Data
Jul. 15, 2009 (IN) .............................. 976/KOL/2009

(51) Int. Cl.
*C07D 265/18* (2006.01)
(52) U.S. Cl.
USPC ........................................ 544/92; 514/230.5
(58) Field of Classification Search
USPC .......................................................... 544/92
See application file for complete search history.

(56) References Cited

U.S. PATENT DOCUMENTS

| | | | |
|---|---|---|---|
| 5,519,021 | A | 5/1996 | Young et al. |
| 5,665,720 | A | 9/1997 | Young et al. |
| 5,814,639 | A | 9/1998 | Liotta et al. |
| 6,028,237 | A | 2/2000 | Parsons, Jr. |
| 6,728,728 | B2 | 4/2004 | Spiegler et al. |
| 2003/0060645 | A1 | 3/2003 | Hu et al. |

FOREIGN PATENT DOCUMENTS

| | | |
|---|---|---|
| EP | 0 517 145 | 1/2002 |
| WO | WO 9964048 A1 * | 12/1999 |
| WO | WO 00/09494 | 2/2000 |
| WO | WO 2009/133538 | 11/2009 |
| WO | WO 2010/032259 | 3/2010 |

OTHER PUBLICATIONS

Caira, "Crystalline Polymorphism of Organic Compounds." *Topics in Current Chemistry*, vol. 198, 1998, pp. 163-208.
Hernandez et al., "Synthesis of 1,4-dihydro-benzo[*d*][1,3]oxazin-2o-ones from Phthalides via an Aminolysis-Hofmann Rearrangement Protocol." *Tetrahedron Letters*, vol. 48, 2007, pp. 8972-8975.
Pedersen et al., "The Flourishing Syntheses of Non-Nucleoside Reverse Transcriptase Inhibitors." *Synthesis*, No. 4, 2000, pp. 479-495.
"Efavirenz." *Drugs of the Future*, vol. 23, No. 2, 1998, pp. 133-141.
International Search Report for Application No. PCT/IN2010/000465 mailed Nov. 12, 2010.

* cited by examiner

*Primary Examiner* — Kahsay Habte
(74) *Attorney, Agent, or Firm* — Merchant & Gould P.C.

(57) ABSTRACT

An improved process for Efavirenz, which has several advantages over reported methods like low cost, high yield, better optical purity and industrial feasibility.

11 Claims, No Drawings

PROCESS FOR PREPARATION OF EFAVIRENZ

This application is a National Stage Application of PCT/IN2010/000465, filed 12 Jul. 2010, which claims benefit of Serial No. 976/KOL/2009, filed 15 Jul. 2009 in India and which applications are incorporated herein by reference. To the extent appropriate, a claim of priority is made to each of the above disclosed applications.

FIELD OF INVENTION

The present invention relates to an improved process for Efavirenz, which has several advantages over reported methods like low cost, high yield, better optical purity and industrial feasibility.

BACKGROUND AND PRIOR ART

Efavirenz chemically known as (−)6-Chloro-4-cyclopropylethynyl-4-trifluoromethyl-1,4-dihydro-2H-3,1-benzoxazin-2-one, is a highly potent non-nucleoside reverse transcriptase inhibitor (NNRTI).

A number of compounds are effective in the treatment of the human immunodeficiency virus (HIV) which is the retrovirus that causes progressive destruction of the human immune system. Effective treatment through inhibition of HIV reverse transcriptase is known for non-nucleoside based inhibitors. Benzoxazinones have been found to be useful non-nucleoside based inhibitors of HIV reverse transcriptase.

(−)6-chloro-4-cyclopropylethynyl-4-trifluoromethyl-1,4-dihydro-2H-3,1-benzoxazin-2-one (Efavirenz) is efficacious against HIV reverse transcriptase resistance. Due to the importance of (−)6-chloro-4-cyclopropylethynyl-4-trifluoromethyl-1,4-dihydro-2H-3,1-benzoxazin-2-one, economical and efficient synthetic processes for its production needs to be developed.

The product U.S. Pat. No. 5,519,021, discloses the preparation of Efavirenz, in Example-6, column-29, involving cyclisation of racemic mixture of 2-(2-amino-5-chlorophenyl)-4-cyclopropyl-1,1,1-trifluoro-3-butyn-2-ol using 1,1'-carbonyldiimidazole as carbonyl delivering agent to give racemic Efavirenz. Further, resolution of the racemic Efavirenz is carried out using (−) camphanic acid chloride to yield optically pure Efavirenz.

However, research article published in the *Drugs of the future*, 1998, 23(2), 133-141 discloses process for manufacture of optically pure Efavirenz. The process involves cyclisation of racemic 2-(2-amino-5-chlorophenyl)-4-cyclopropyl-1,1,1-trifluoro-3-butyn-2-ol using 1,1-carbonyldiimidazole as carbonyl delivering agent to give racemic Efavirenz and further resolution by (−) camphanic acid chloride.

Similarly research article published in *Synthesis* 2000, No. 4, 479-495 discloses stereoselective synthesis of Efavirenz (95% yield, 99.5% ee), as shown below

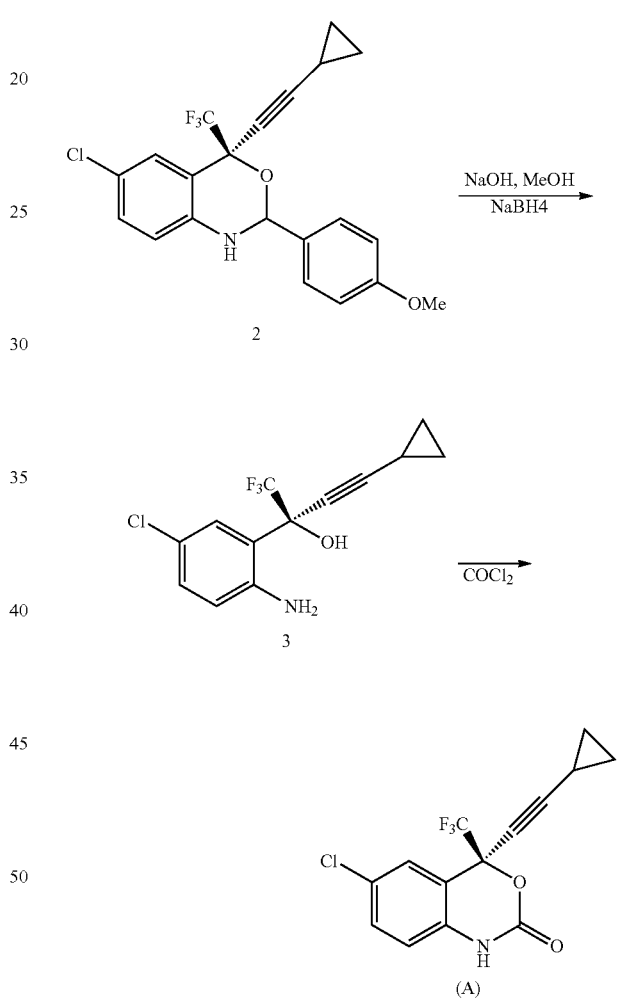

Even though many prior art processes report method for the preparation of Efavirenz, each process has some limitations with respect to yield, purity, plant feasibility etc. Hence in view of the commercial importance of Efavirenz there remains need for an improved process.

The applicants of the present invention have developed an improved process for synthesis of optically pure (−)6-chloro-4-cyclopropylethynyl-4-trifluoromethyl-1,4-dihydro-2H-3,1-benzoxazin-2-one of the formula (A)

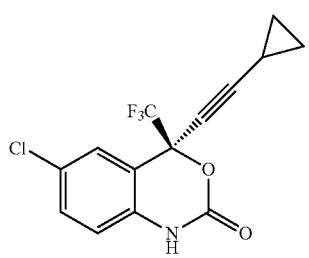

(A)

SUMMARY OF THE INVENTION

In one embodiment of the present invention, there is provided a process for cyclisation of the optically pure (S)-2-(2-amino-5-chlorophenyl)-4-cyclopropyl-1,1,1-trifluoro-3-butyn-2-ol using carbonyl group delivering agents like Triphosgene, Carbonyldiimidazole and Diphenylcarbonate.

In another embodiment of the present invention, there is provided a process to obtain optically pure Efavirenz by the cyclisation of the optically pure (S)-2-(2-amino-5-chlorophenyl)-4-cyclopropyl-1,1,1-trifluoro-3-butyn-2-ol using carbonyl group delivering agents like Triphosgene, Carbonyldiimidazole and Diphenylcarbonate.

DETAIL DESCRIPTION OF THE INVENTION

The present invention provides an improved process for Efavirenz by cyclising the optically pure 2-(2-amino-5-chlorophenyl)-4-cyclopropyl-1,1,1-trifluoro-3-butyn-2-ol by the following reaction sequence:

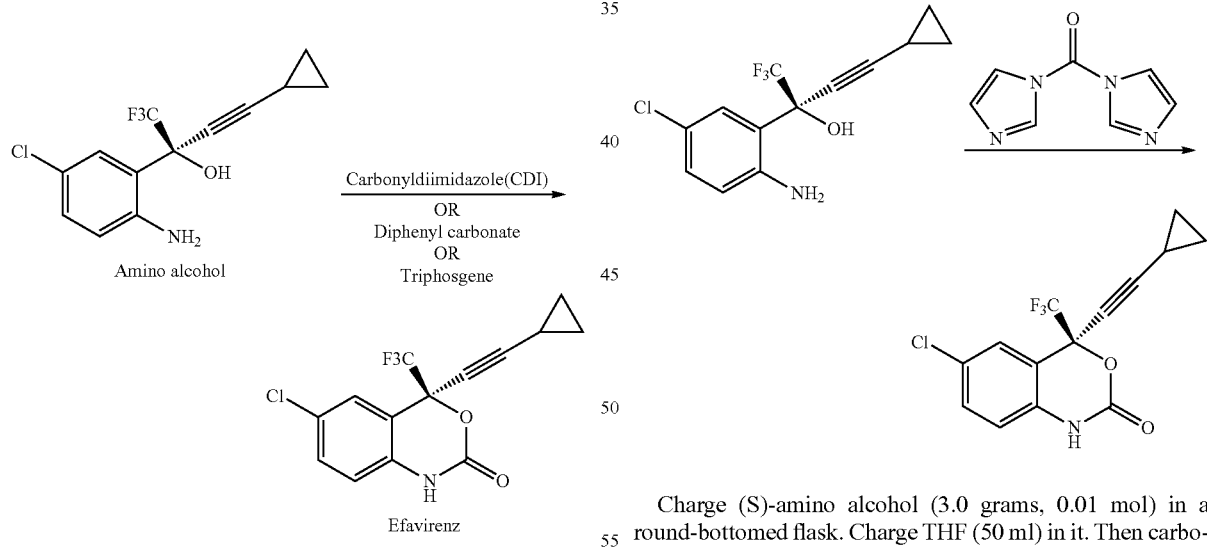

The optically pure (S)-2-(2-amino-5-chlorophenyl)-4-cyclopropyl-1,1,1-trifluoro-3-butyn-2-ol (amino alcohol) is reacted with carbonyl delivering agent and undergo cyclisation to give optically pure (−)6-Chloro-4-cyclopropylethynyl-4-trifluoromethyl-1,4-dihydro-2H-3,1-benzoxazin-2-one (Efavirenz). The carbonyl delivering agents are selected from Triphosgene, Carbonyldiimidazole and Diphenylcarbonate.

The inventors of the present invention have observed that the use of Carbonyldiimidazole and Diphenylcarbonate is clean and plant feasible. Also these reagents are commercially available. Further more, the carbonyldiimidazole used can be regenerated and reused, thereby making the process cost effective.

The major advantage of the present improved process is high yield and low cost.

The reported methods for such reactions have disclosed use of phosgene gas, which is not only toxic but also not usable at plant scale.

Similarly prior art process involves resolution of racemic Efavirenz which follows number of steps and ultimately results in poor yield.

The experimental approach towards the present invention shows that the reaction condition changes with change in the carbonyl group delivering agent.

The reaction is carried out in presence of aprotic solvent and is highly dependent on the temperature of the reaction medium.

The temperature used for the reaction is −10° C. to 60° C.

The aprotic solvent used for the reaction is tetrahydrofuran.

As mentioned above, the reference *Synthesis* 2000, No. 4, 479-495 discloses similar process as claimed herein; however the improvement comprises use of economical and plant feasible carbonyl delivering agents.

The invention is further illustrated by following examples—

Example-1

Preparation of Efavirenz From (S)-Amino Alcohol by Using Carbonyldiimidazole

Charge (S)-amino alcohol (3.0 grams, 0.01 mol) in a round-bottomed flask. Charge THF (50 ml) in it. Then carbonyldiimidazole (8.2 grams, 0.05 mol) was added in it in one lot. Slowly heated to 55° C., monitored by TLC/HPLC. After completion of reaction, the solvent was evaporated at 35-40° C. Ethylacetate (100 ml) & DMW (135 ml) was added, stirred, settled & layer was separated. To the aqueous layer ethyl acetate (100 ml) was added & stirred, settled & layer was separated. Combined organic layers was washed with 2% hydrochloric acid solution (40 ml×2), saturated sodium bicarbonate (50 ml) & 10% brine solution (50 ml). The final organic layer was concentrated & crystallized from n-Heptane to get 92-98% yield of pure Efavirenz (HPLC purity=99.7%).

Example-2

Preparation of Efavirenz From (S)-Amino Alcohol by Using Diphenylcarbonate

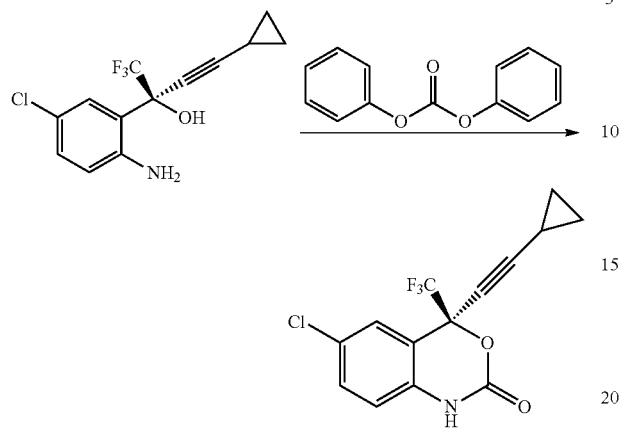

1.5 g of (S)-amino alcohol (5.19 mmol) was dissolved in THF (20 ml) and DBU (1.7 ml, 11.42 mmol) was added at room temperature. Then diphenylcarbonate (4.443 g, 19.38 mmol) was added and the mixture was further stirred at 60° C. for 2 h. The reaction mixture was diluted with water and extracted with ethyl acetate. The organic layer was successively washed with aqueous hydrochloric acid, DM water and brine, concentrated and purified on silica gel column chromatography to get 90-98% yield of pure Efavirenz (HPLC purity=99.7%).

Example-3

Preparation of Efavirenz from (S)-Amino alcohol by Using Triphosgene

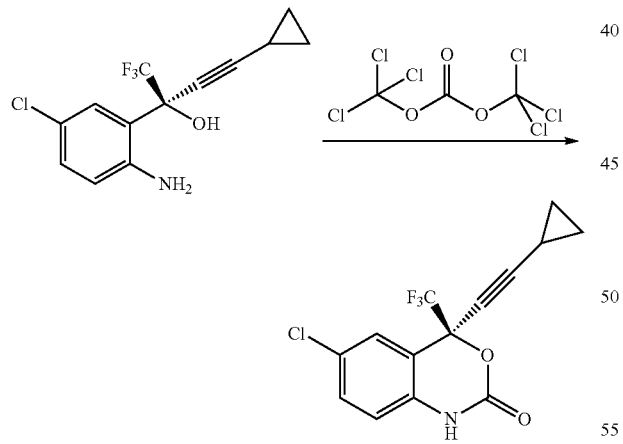

(S)-Amino alcohol (5.0 grams, 17.30 mmol) was dissolved in n-heptane (15 ml) & tetrahydrofuran (7.0 ml) & cooled to −10° C. Triphosgene (2.57 grams, 8.65 mmol) was dissolved in 12 ml tetrahydrofuran and added drop wise over a period of 1.0 hour keeping the reaction temperature below 0° C. The slurry was warmed to room temperature & stirred further for 1.0 hour. Methanol (2.6 ml) was added & stirred for 0.5 hour, n-heptane (30 ml) was added & then 40 ml of solvent was removed on rotavapour under vacuum. Again n-heptane (30 ml) & tetrahydrofuran (7.5 ml) was added to the reaction mass. To the solution 5% aqueous sodium bicarbonate (40 ml) was added & stirred further for 2.0 hours at room temperature. The organic layer was separated & washed with DM Water (40 ml). The organic layer was warmed to 50° C., filtered & rinse with n-heptane (40 ml) & concentrated on rotavapour. The residue was crystallized from n-heptane to get 4.0 grams (yield=74%) of Pure Efavirenz.

The invention claimed is:

1. A process for preparation of optically pure (−)6-chloro-4-cyclopropylethynyl-4-trifluoromethyl-1,4-dihydro-2H-3,1-benzoxazin-2-one having formula:

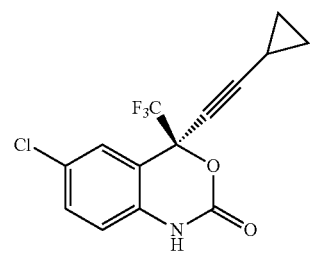 [SMILES: O=C1Nc2ccc(Cl)cc2[C@@](C#CC2CC2)(C(F)(F)F)O1]

the process comprising reacting optically pure (−)2-(2-amino-5-chlorophenyl)-4-cyclopropyl-1,1,1-trifluoro-3-butyn-2-ol, of formula

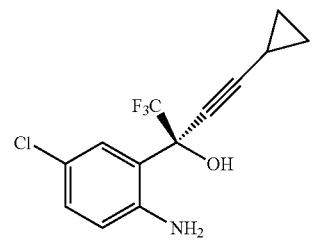 [SMILES: Nc1ccc(Cl)cc1[C@@](O)(C#CC1CC1)C(F)(F)F]

with a carbonyl delivering agent in tetrahydrofuran to give optically pure (−)-6-chloro-4-cyclopropylethynyl-4-trifluoromethyl-1,4-dihydro-2H-3,1-benzoxazin-2-one.

2. The process according to claim 1, wherein the carbonyl delivering agent is selected from:

Carbonyldiimidazole

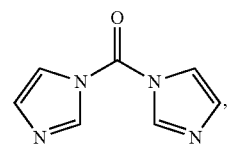 [SMILES: O=C(n1ccnc1)n1ccnc1]

Diphenylcarbonate

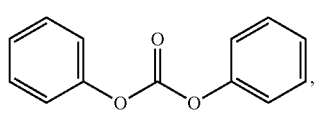

or

Triphosgene

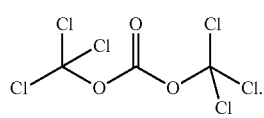

3. The process according to claim 1, wherein the carbonyl delivering agent is carbonyldiimidazole.

4. The process according to claim 1, wherein the carbonyl delivering agent is diphenylcarbonate.

5. The process according to claim 1, wherein the carbonyl delivering agent is triphosgene.

6. The process according to claim 3, wherein the reaction temperature is 60° C.

7. The process according to claim 4, wherein the reaction temperature is 60° C.

8. The process according to claim 5, wherein the reaction temperature is −10° C.

9. A process for preparation of optically pure (−)6-chloro-4-cyclopropylethynyl-4-trifluoromethyl-1,4-dihydro-2H-3,1-benzoxazin-2-one having formula:

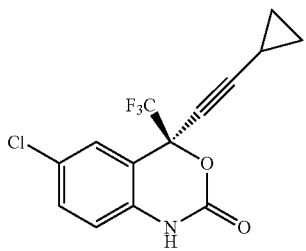 [SMILES: O=C1Nc2ccc(Cl)cc2[C@@](C#CC2CC2)(C(F)(F)F)O1]

the process comprising the step; reacting optically pure (−)2-(2-amino-5-chlorophenyl)-4-cyclopropyl-1,1,1-trifluoro-3-butyn-2-ol, of formula

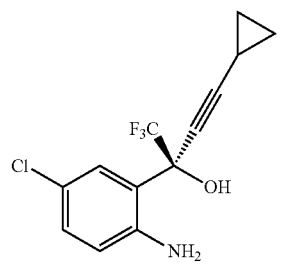 [SMILES: Nc1ccc(Cl)cc1[C@@](O)(C#CC1CC1)C(F)(F)F]

with a carbonyl delivering agent in an aprotic solvent, to give optically pure (−)-6-chloro-4-cyclopropylethynyl-4-trifluoromethyl-1,4-dihydro-2H-3,1-benzoxazin-2-one;

wherein the carbonyl delivering agent is diphenylcarbonate or triphosgene.

10. The process of claim 9, wherein the carbonyl delivering agent is diphenyl carbonate and the reaction temperature is 60° C.

11. The process of claim 9, wherein the carbonyl delivering agent is triphosgene and the reaction temperature is −10° C.

* * * * *